US009468662B2

(12) United States Patent
Laruelle et al.

(10) Patent No.: US 9,468,662 B2
(45) Date of Patent: *Oct. 18, 2016

(54) USE OF THE PAT NONAPEPTIDE IN THE TREATMENT AND PREVENTION OF NEURODEGENERATIVE DISEASES

(71) Applicant: ORPHIT, Saint-Laurent-du-Var (FR)

(72) Inventors: Claude Laruelle, Villeneuve-Loubet (FR); Jamal Temsamani, Nimes (FR); Frederic Mourlane, Nice (FR)

(73) Assignee: ORPHIT, Saint-Laurent-du-Var (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/929,449

(22) Filed: Nov. 2, 2015

(65) Prior Publication Data
US 2016/0074463 A1   Mar. 17, 2016

Related U.S. Application Data

(63) Continuation-in-part of application No. 13/809,805, filed as application No. PCT/FR2011/000410 on Jul. 11, 2011, now Pat. No. 9,192,654.

(30) Foreign Application Priority Data

Jul. 12, 2010   (FR) ...................... 10 02965

(51) Int. Cl.
 *A61K 38/08*   (2006.01)
 *A61K 9/00*    (2006.01)
(52) U.S. Cl.
 CPC ............. *A61K 38/08* (2013.01); *A61K 9/0019* (2013.01)

(58) Field of Classification Search
None
See application file for complete search history.

(56) References Cited

U.S. PATENT DOCUMENTS

| 5,112,810 A | 5/1992 | Nagai et al. |
|---|---|---|
| 2005/0261194 A1 | 11/2005 | Dardenne et al. |
| 2006/0159626 A1 | 7/2006 | Frey, II |
| 2008/0306048 A1 | 12/2008 | Kaplan et al. |
| 2011/0098223 A1 | 4/2011 | Temsamani et al. |

FOREIGN PATENT DOCUMENTS

| CA | 2026306 | 4/1991 |
|---|---|---|
| EP | 0425828 | 5/1991 |
| FR | 2830451 | 4/2003 |
| FR | 2930156 | 10/2009 |

OTHER PUBLICATIONS

Hoke 2009 "insearch of novel treatments for peripheral neuropathies and nerve regeneration" accessed from discoverymedicine.com on Feb. 19, 2016.*
Bachem "Peptide calculator" accessed from www.bachem.com on Dec. 18, 2014.

(Continued)

*Primary Examiner* — Adam M Weidner
(74) *Attorney, Agent, or Firm* — Young & Thompson

(57) ABSTRACT

A PAT nonapeptide of formula EAKSQGGSD (SEQ ID NO: 1) can be used to treat or prevent neurodegenerative diseases such as Alzheimer's disease, Parkinson's disease, Huntington's disease and amyotrophic lateral sclerosis. Pharmaceutical compositions containing the PAT nonapeptide can be formulated for administration by parenteral route, including the subcutaneous, intraperitoneal, intravenous or intranasal routes.

11 Claims, 10 Drawing Sheets

Measurement of spontaneous alternation during the Y maze test. The PAT peptide is injected by intra-cerebroventricular (i.c.v.) route.

(56) References Cited

OTHER PUBLICATIONS

Innovagen "Peptide property calculator" accessed from www.innovagen.com on Dec. 18, 2014.
Wikipedia.org "Route of Administration" accessed from en.wikipedia.org on Dec. 17, 2014.
Dictionary.com "Perenteral" accessed from dictionary.reference.com on Dec. 17, 2014.
Reggiani et al. 2006 "Gene therapy for long-term restoration of circulating thymulin in thymectomized mice and rats" Gene therapy 13:1214-1221.
Hansch et al., "Exploring QSAR Fundamentals and Applications in Chemistry and Biology", ACS Professional Reference Book, American Chemistry Society, Washington, DC 1995, pp. 388-409.
Pajouhesh et al., "Medicinal Chemical Properties of Successful Central Nervous System Drugs", The Journal of the American Society for Experimental NeuroTherapeutics, vol. 2, No. 4, Oct. 2005, pp. 541-553.
Reichel, "The Role of Blood-Brain Barrier Studies in the Pharmaceutical Industry", Current Drug Metabolism, 2006, 7 183-203.
Lennard et al. 2000 "interleukin-1 beta, interleukin-5, interleukin-6, interleukin-8, and tumor necrosis factor-alpha in chronic sinusitis: response to systemic corticosteroids" Am J Rhinol 14(6):367-73.
Rafii and Aisen 2009 "Recent developments in Alzheimer's disease therapeutics" BMC medicine 7:7.
B. Safieh-Garabedian et al., "Thymulin reverses inflammatory hyperalgesia and modulates the increased concentration of proinflammatory cytokines induced by i.c.v. endotoxin injection", Neuroscience, vol. 121, No. 4, (2003), pp. 865-873.
G.R. Morel et al., "Peripheral and mesencephalic transfer of a synthetic gene for the thymic peptide thymulin", Brain Research Bulletin, vol. 69, No. 6, (May 31, 2006), pp. 647-651.
J.J. Haddad et al., "Thymulin: An emerging anti-inflammatory molecule", Current Medicinal Chemistry—Anti-Inflammatory & Anti-Allergy Agents, vol. 4, No. 3, (Jun. 2005), pp. 333-338.
F. Licastro et al., "Zinc and thymic hormone-dependent immunity in normal ageing and in patients with senile dementia of the Alzheimer type", Journal of Neuroimmunology, vol. 27, No. 2-3, (May 1, 1990), pp. 201-208.
L.J. Davis et al., "Plasmatic activity of thymulin: Comparison of free and protein bound thymulin in Alzheimer's disease", Advances in the Biosciences; Alzheimer's Disease and Related Disorders, (Jul. 12-17, 1993), pp. 279-280.

* cited by examiner

Figure 1: Measurement of spontaneous alternation during the Y maze test. The PAT peptide is injected by intra-cerebroventricular (i.c.v.) route.
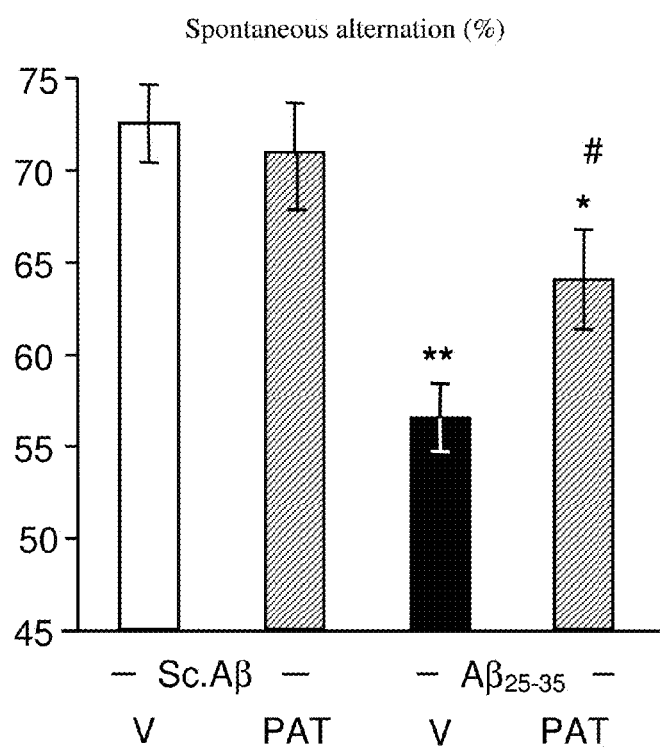

Figure 2A: Passive avoidance test: measurement of latency time to enter in the dark compartment. Injection of the PAT peptide (5μg) by i.c.v. route.
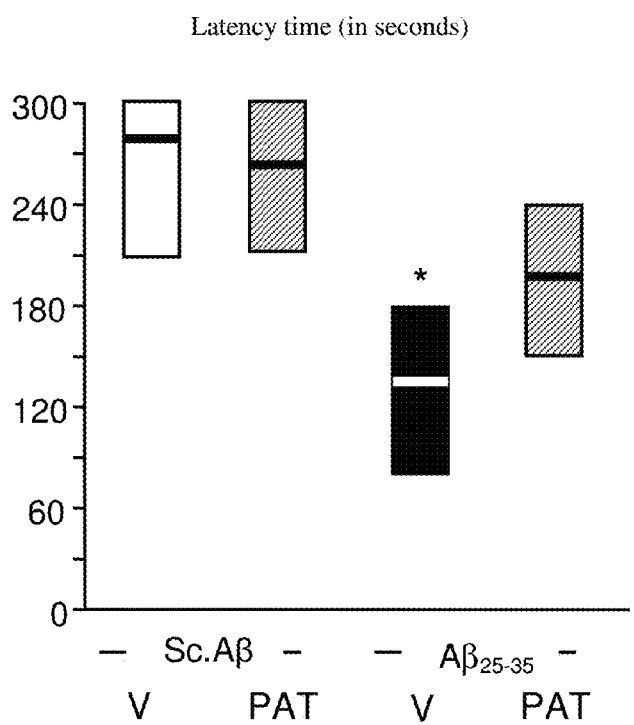

Figure 2B: Passive avoidance test: measurement of latency time for the escape. Injection of the PAT peptide (5µg) by i.c.v. route.
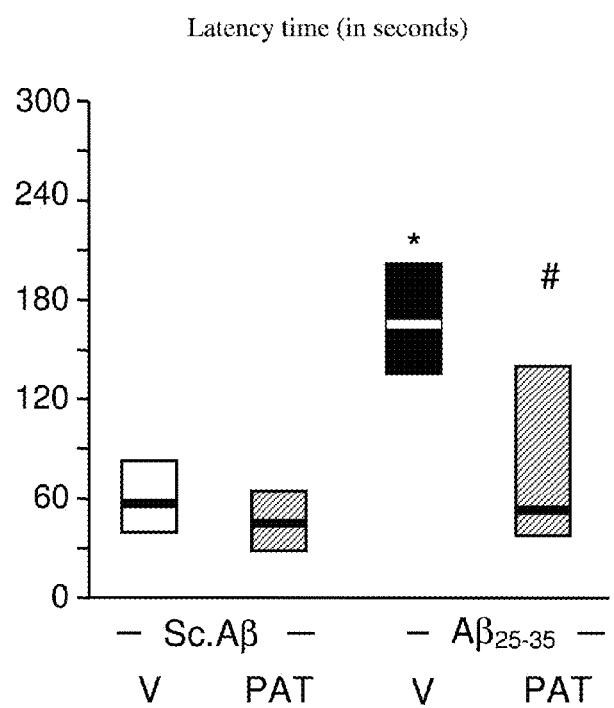

Figure 3: Y-maze test: measurement of spontaneous alternation. Injection of the PAT peptide by intra-peritoneal (i.p..) route.
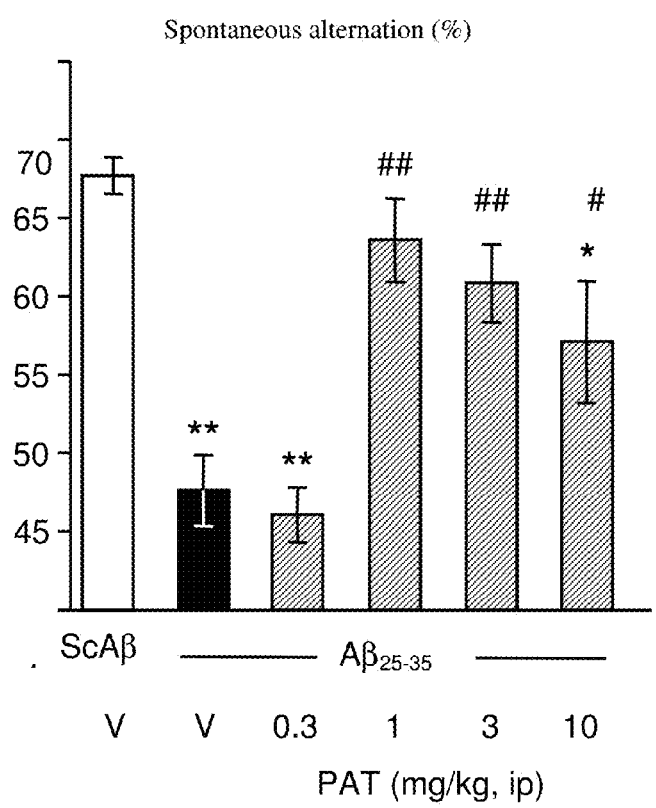

Figure 4A: Passive avoidance test: measurement of latency time to enter in the dark compartment. Injection of the PAT peptide using i.p. route.
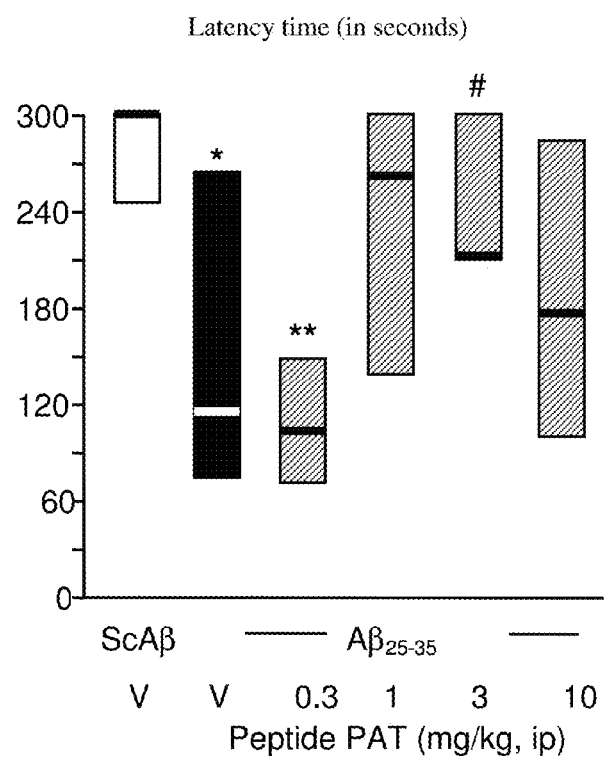

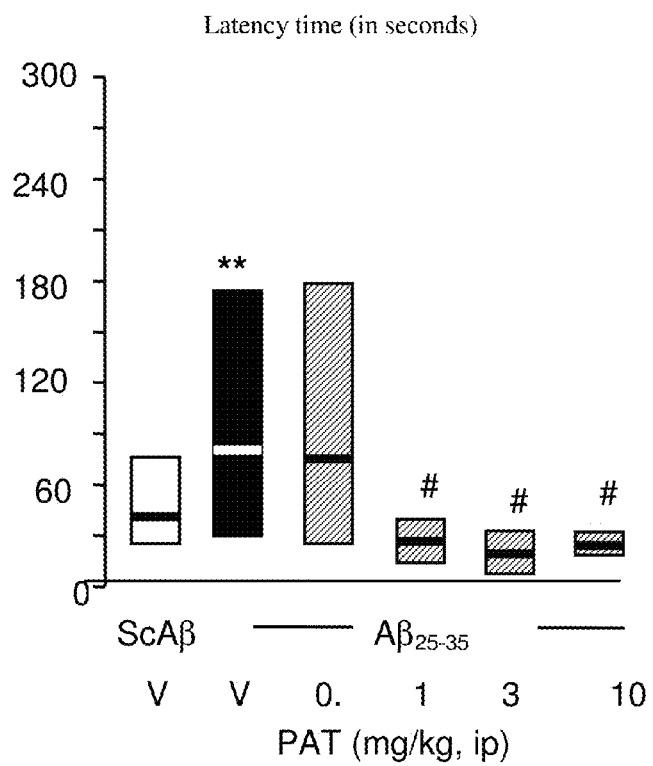
Figure 4B. Passive avoidance test: measurement of latency time for escape. Injection of the PAT peptide by i.p. route.

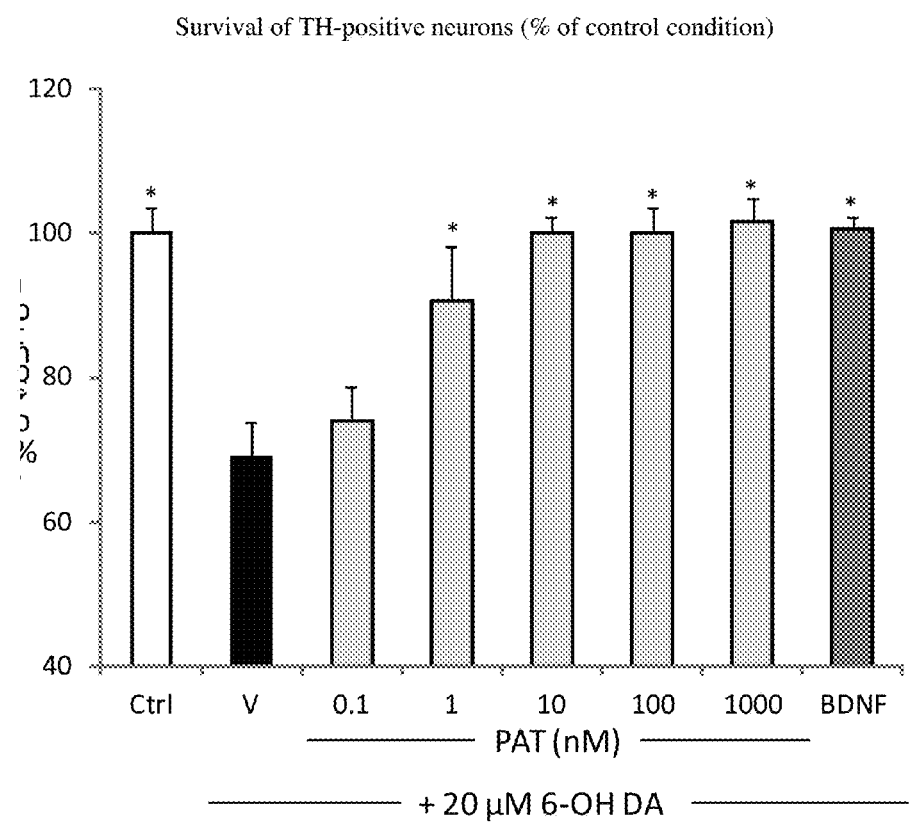
Figure 5A: Effect of PAT (1 h pretreatment, different concentrations) on the survival of TH-positive neurons injured by 6-OHDA (20 µM, 24 h).

Figure 5B: Microscopic aspect of dopaminergic neurons maintained in culture conditions (Ctrl), injured with 6-OHDA (+20 µM 6OHDA) or pretreated with 10 nM PAT before 6-OHDA injury (+20 µM 6OHDA + 10 nM PAT). Dopaminergic neurons were stained with TH-specific monoclonal antibody.
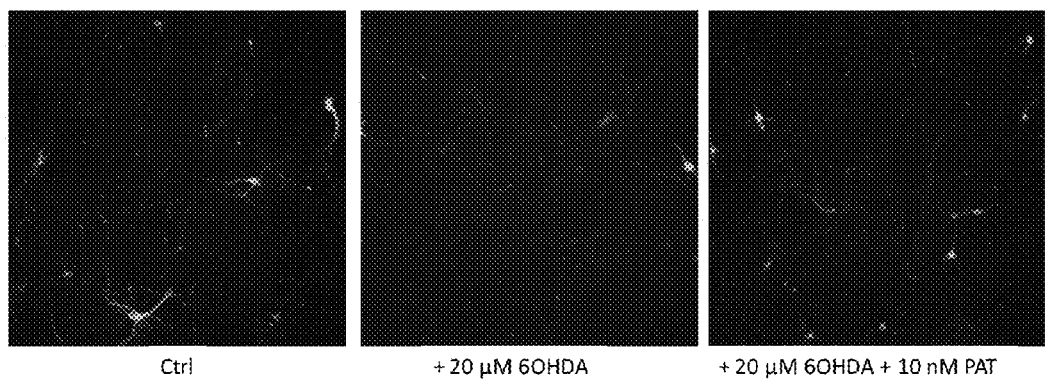

Figure 6A: Effect of PAT (1 h pretreatment, different concentrations) on the survival of GAD67-positive medium spiny neurons injured by glutamate (10 µM, 24 h).
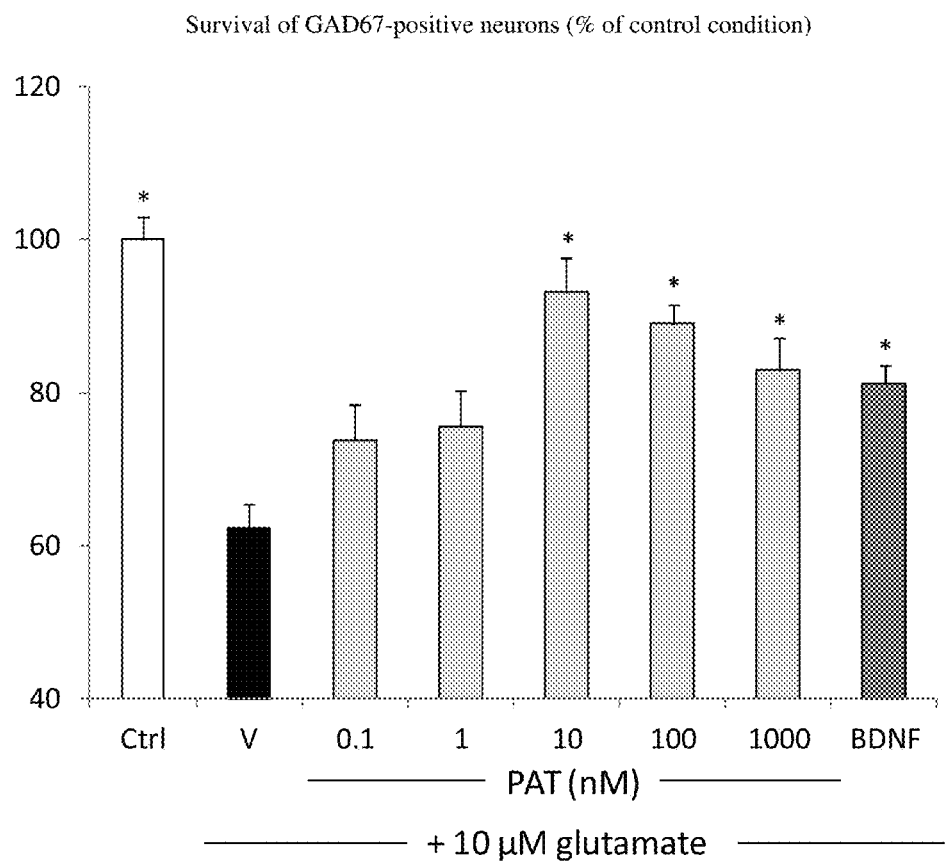

Figure 6B: Microscopic aspect of GABAergic medium spiny neurons maintained in culture conditions (Ctrl), injured with glutamate (+10 µM glutamate) or pretreated with 10 nM PAT before glutamate injury (+10 µM glutamate + 10 nM PAT). GABAergic medium spiny neurons were stained with GAD67-specific monoclonal antibody.
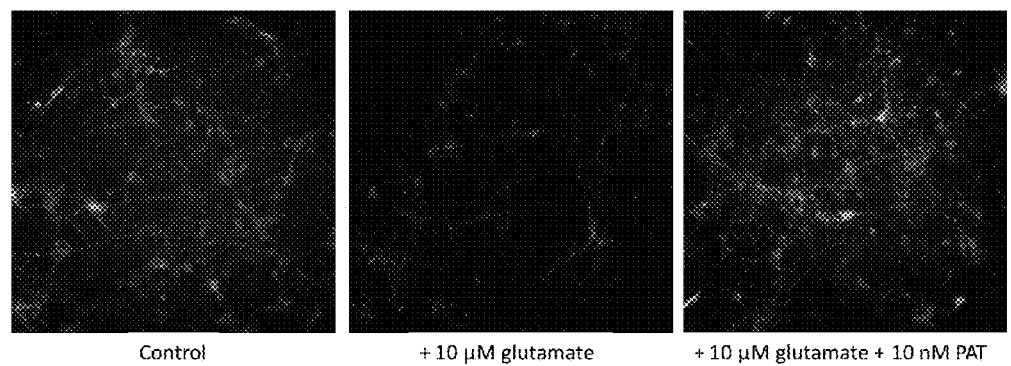

SEQUENCE LISTING

<160> NUMBER OF SEQ ID NOS: 1

<210> SEQ ID NO 1
<211> LENGTH: 9
<212> TYPE: PRT
<213> ORGANISM: Artificial Sequence
<220> FEATURE:
<223> OTHER INFORMATION: Peptide Analog of Thymulin nonapeptide

<400> SEQUENCE: 1

Glu Ala Lys Ser Gln Gly Gly Ser Asp
1               5

USE OF THE PAT NONAPEPTIDE IN THE TREATMENT AND PREVENTION OF NEURODEGENERATIVE DISEASES

SEQUENCE LISTING

An attached Sequence Listing (i. Name: SEQ_LISTING, ii. Date of Creation: Nov. 18, 2015, and iii. Size: 1 KB) is submitted herewith.

FIELD OF THE INVENTION

The invention concerns the use of the PAT nonapeptide for the manufacturing of a drug in the treatment or the prevention of neurodegenerative diseases such as Alzheimer's disease, Parkinson's disease, Huntington's disease or amyotrophic lateral sclerosis.

BACKGROUND OF THE INVENTION

The neurodegenerative diseases affect progressively the brain function and more generally the nervous system. The process involved consists generally in a deterioration of the functioning of the nervous cells, in particular the neurons, leading to the cellular death. The consequence for the patient is a progressive alteration, usually irreversible, of the nervous functions which can induce his death. The clinical outcome can be either some damages of the psychic function, leading to dementia such as in Alzheimer's or Pick's disease, or motor abnormalities such as in amyotrophic lateral sclerosis or Parkinson's disease, or the combination of both such in Huntington's chorea disease or Creutzfeldt-Jacob's disease.

Alzheimer's disease (AD) is the most known and spread of the neurodegenerative diseases. It is characterized by memory loss and sometimes by disorders of reasoning, organization, language and perception. It is widely admitted that the AD symptoms arise from an increase of the production or accumulation of a specific protein (β-amyloid) in the brain, which leads to the death of nervous cell. Increasing age is the greatest know risk factor for AD. Approximately 30 millions of people in the world are affected by AD. Population ageing suggests that the economic burden caused by AD disease will become increasingly important.

Parkinson's disease (PD) is the second most common neurodegenerative disorder in the United States and approximately 1-2% of worldwide population older than 65 years suffers from this progressive disease (Dorsey E R. et al. Neurology 2007; 68: 384). The predominant motor symptoms of PD including slow movement, resting tremor, rigidity and gait disturbance are caused by the loss of dopaminergic neurons in the substantia nigra. Although the etiology of PD remains so far unknown, both genetic and environmental factors appear to play a role (Paisan-Ruiz C. et al. Neuron. 2004; 44: 595 and Vila M. and Przedborski S. Nat. Med. 2004; Suppl 10: S58).

Huntington's disease (HD) is an autosomal dominant inherited and progressive neurodegenerative disease that affects approx. 30,000 individuals in the US (about 200,000 individuals are at risk) (Harper P S. Hum. Genet. 1992; 89: 365). HD is clinically characterized by abnormal involuntary movements, behavioral disturbance, cognitive dysfunction and psychiatric disease. Massive loss of GABAergic medium spiny neurons (MSNs) of the striatum occurs in the HD brain together with enlargement of the ventricles and a corresponding shrinkage of the overlying cortex. MSNs of the striatum project into various regions of the CNS and are the key drivers of the progression of degenerative process that involves the remainder of the basal ganglia and subsequent dissemination including cortex and substantia nigra (Andric J. et al. Neurosci. Lett. 2007; 416: 272 and Frank S et al. Neurology. 2004; 62: A204). Dopamine, glutamate and γ-aminobutiric acid (GABA) are thought to be the most affected neurotransmitters in HD (Gunawardena S. et al. Arch. Neurol. 2005; 62: 46).

Amyotrophic lateral sclerosis (ALS) is an adult-onset neurodegenerative disorder characterized by selective motor neuron death. Both upper motor neurons in the motor neuron cortex and lower motor neurons in the brainstem and in the ventral horn of the spinal cord are affected. Patients develop a progressive muscle phenotype characterized by spasticity, hyperreflexia, fasciculations, muscle atrophy and paralysis. ALS is usually lethal within 3 to 5 years after diagnosis, only 5-10% of patients survive beyond 10 years. There are approximately 140,000 new cases diagnosed worldwide each year. In most cases (90%) there is no family history of ALS. However a clear family history is present in 10% of patients who then suffer from familial ALS. Although the familial ALS is in almost all cases inherited in an autosomal dominant way, autosomal recessive and X-linked forms exist. Mutations in more than 10 different genes are known to cause familial ALS. Many mechanisms have been suggested to play a role in the pathogenesis and disease progression. These include amongst others neuronal excitotoxicity, mitochondrial dysfunction, deregulated autophagy, axonal transport dysfunction and refraction (Cudkowicz M E Ann. Neurol. 1997 41, 210-221).

Albeit, there is currently no treatment leading to the AD recovery, there are 2 types of drugs which can decrease its symptoms and slow down its evolution. EP236684A, DE 3805744A and EP296560A disclose drugs based on acetylcholinesterase inhibitors: galantamine, rivastigmine and donepezil respectively. EP392059A discloses a drug containing memantine which is a NMDA receptor antagonist. All these drugs have received a marketing authorization to treat AD. However, the treatment only affects the symptoms. Several studies have shown that these drugs slow down only in a modest way the progression of cognitive symptoms as well as erratic behaviors in some patients. Moreover, half of the patients who received these drugs do not respond to these treatments. Finally, these drugs induce several undesirable effects such as nausea, diarrhea, hepatic disorders etc. . . . . . Thus, there is an urgent need for drugs with a new mechanism of action different from the aforementioned drugs. Several projects are being explored currently. Few examples are mentioned hereafter.

The secretase inhibitors block the transformation process of the β-amyloid protein precursor (known as "APP") into the β-amyloid protein and thus permit to slow down its dangerous accumulation in the brain. Among these inhibitors is the tramiprosate (ALZHEMED®) which was tested in a phase II clinical study (Aisen P S et al. Neurology 2006; 28: 1757). Another inhibitor, the scillo-cyclohexanehexol, was tested in animals successfully (MacLarin J A et al. Nat. Med. 2006; 12: 801). These molecules interact with β-amyloid proteins during their formation and prevent them from agglomerating and from forming small aggregates, which destroy nervous cells by settling as solid plaques. However, they already cause important damage during their formation.

Other treatments such as ubiquitin (compound naturally produced in the brain) induce the disappearance of β-amyloid protein before its reaches high accumulation in the brain (Taddei N. et al. Neurosci. Lett. 1993; 151: 158). However, the ubiquitin rates remain insufficient in patients which suffer from Alzheimer's disease.

Another interesting method is the immunological approach. WO 94/06476A discloses a new type of drug which has a target different from the molecules cited previously: Etanercept (ENBREL®), which is a fusion protein directed against the TNF-α pro-inflammatory cytokine A recent pilot study was carried out over a 6 months period and showed encouraging results in term of cognitive improvement (Tobinick E. CNS Drugs 2009; 23: 713). In addition to the fact that the project is at a preliminary phase at the clinical level, the administration of the product ENBREL® was carried out by perispinal route in order to circumvent the problem linked to its incapacity to pass across the blood-brain barrier (BBB) (Griffin S. Newspaper of Neuroinflammation; 2008; 5: 3). However, this route of administration is burdensome and painful for the patient and requires a certain number of precautions: it must be carried out in hospitals. The presence of the blood-brain barrier (BBB) restricts strongly the passage of molecules such as ENBREL® from the plasma into the cerebral extracellular medium: very few drugs designed in laboratories, cross this barrier to treat brain diseases.

Limited therapeutic options are available to PD, HD and ALS patients as only symptomatic treatments have received marketing authorizations so far. The major challenge for clinical development of new drug entities in neurodegenerative disorders lies in the difficulty to identify and hit disease-relevant targets that will beneficially interfere with complex physiopathological mechanisms. Moreover such therapeutic agent must cross the BBB and reach diseased regions of the central nervous system. U.S. Pat. Nos. 4,900,755 and 6,238,699 disclose an oral formulation for the controlled release of the combination of levodopa/carbidopa (SINEMET®). This treatment compensates for the loss of dopaminergic neurons that occurs in PD brains. Carbidopa, a decarboxylase inhibitor, prevents peripheral metabolism of levodopa, the precursor of dopamine, outside of the brain. In the brain levodopa is broken down into dopamine which increases dopamine concentration in the striatum. Levodopa, dopamine precursor is used because the natural neurotransmitter does not cross the BBB. Tetrabenazine (XENAZINE®) is an oral dopamine-depleting agent that treats chorea associated with HD. Dopamine is required for fine motor movement, so the inhibition of its transmission is efficacious for hyperkinetic movement. Tetrabenazine is a reversible human vesicular monoamine transporter type 2 inhibitor. It acts within the basal ganglia and promotes depletion of monoamine neurotransmitters serotonin, norepinephrine, and dopamine from stores. It also decreases uptake into synaptic vesicles (Guay D. Am. J. Geriatr. Pharmacother. 2010; 8: 331). Finally, riluzole (RILUTEK®) is the only approved treatment for ALS which increases lifespan by only 2-3 months after 1.5 years of treatment, and is effective at delaying the use of assisted mechanical ventilation in bulbar patients (Miller R G et al. Neurology 2009; 73: 1218 and Bellingham M C. CNS Neurosci. Ther. 2011; 17: 4). Pharmacological properties of riluzole include an inhibitory effect on glutamate release mediated by inactivation of voltage-dependent sodium channels and by its ability to interfere with intracellular events that follow transmitter binding at excitatory amino acid receptors. Although these drugs reduce cognitive or motor symptoms and improve quality of life, they fail to modify or halt disease progression. Their long-term use is associated with side-effects that often require treatment arrest.

Therefore, there is a need for drugs which should at the one hand be sufficiently effective to treat AD, PD, HD or ALS and on the other hand cross the BBB. The Applicant objective is to develop a drug capable to treat of Alzheimer's disease and other neurodegenerative disorders without presenting the disadvantages of the existing treatments. The Applicant has found, in a fortuitous way, due to the work already carried out with this molecule, that a peptide analog of thymulin hormone has an interesting potential in the prevention and the treatment of AD, PD, HD and ALS.

We know since the late 1950's the central role played by the thymus in the differentiation of T-cells, responsible in particular of transplant rejection and implicated in the immune defense against the viruses and some bacteria. The hormone secreted by the thymus was then identified as a peptide of 9 amino-acids: the thymulin (Pleau J M et al. Immunol. Lett, 1979; 1:179; Amor et al, Annals Rheum. Dis. 1987; 46: 549). The thymulin effects on the immune system were shown to be zinc-dependent. Indeed, zinc confers to the thymulin a tetrahedral conformation which corresponds to the active form of the molecule. In the absence of zinc, thymulin is no longer active on the immune system. Work was undertaken specifically on a nonapeptide called "PAT" having the sequence of amino-acids Glu-Ala-Lys-Ser-Gln-Gly-Gly-Ser-Asp (EAKSQGGSD). The application WO 03/030927A reports that several derivatives of thymulin, such as the PAT nonapeptide presents analgesic and anti-inflammatory properties, and can treat in pain including neurogenic pain. More recently, the application WO 2009/150310A describes specifically the use of the PAT nonapeptide in the treatment of autoimmune diseases such as rheumatoid arthritis, and intestinal bowel diseases (IBD) such as Crohn's disease and hemorrhagic rectocolitis.

SUMMARY OF THE INVENTION

The present invention refers to the use of the PAT nonapeptide corresponding to the formula (I):

or one of its pharmaceutically acceptable salts in the preparation of a drug in the treatment and the prevention of neurodegenerative diseases, in particular Alzheimer's disease Parkinson's disease, Huntington's disease and amyotrophic lateral sclerosis.

The PAT peptide is administered to the human or the animal at a dose ranging between 0.1 and 50 mg; and preferably between 1 and 10 mg. By "pharmaceutically acceptable salt", one understands as example and in a nonrestrictive way acetate, sulfate or hydrochlorate. The invention also relates to the use of a compound of formula (I) in which one or more amino-acids are in the D configuration.

The pharmaceutical composition of the invention can be administered by parenteral, topical, oral, perlingual, rectal or intraocular route. The preferred administration route is the parenteral route, and in particular the cutaneous (s.c.), intranasal, intra-peritoneal (i.p.) or intravenous (i.v.) routes. It can also be considered a topical route, in particular transderrmal, such as for example, as a patch, pomade or gel.

During an experiment carried out for the invention, it was shown that the PAT nonapeptide displays a biological activity when it is administered by intracerebroventricular (i.c.v.) route—which bypasses the BBB, and also by parenteral route (intra-peritoneal). This latter mode of administration highlights the fact that the product crosses the BBB and reaches the brain. To cross the BBB, persons skilled in the art know that the molecular and physicochemical properties of the molecule must fulfill the 5 criteria described by Lipinski et al. (1997). Adv Drug Del Rev 23: 3-25 (amongst them a low molecular weight, its hydrophobicity, its charge etc. . . . ). Yet, we were surprised to notice that the PAT peptide, which does not fulfill all these criteria, crosses the BBB.

The formulations to be administered by parenteral route contain a solvent allowing the solubilization of a peptide such as the PAT peptide; this solvent can be selected among the water for injection or physiological saline solution, optionally with preservative agents (such as cresol, phenol, benzyl alcohol or methylparaben) and/or buffer agents, and/or isotonic adjuvants and/or surfactants well-known by persons skilled in the art.

One of the preferred administrations is the subcutaneous (s.c.) route. The injectable form by subcutaneous route according to the invention contains the PAT peptide dissolved in an appropriate solvent, with if necessary other excipients such as those cited previously. One of the injectable subcutaneous forms according to the invention contains a polymer which allows a slow diffusion of the PAT peptide during the time course (period up to 30-40 days). In order to achieve that, PAT peptide is dissolved in an appropriate solvent such as a physiological saline solution, and mix with appropriate polymers such as the polyethylene glycols, polyvinyl pyrrolidones and polyacrylamides.

BRIEF DESCRIPTION OF THE DRAWINGS

Other advantages and characteristics of the invention will become clear upon reading the following examples. Reference is made to the appendix drawings in which:

FIG. 1 shows the results obtained from Y-maze test in mice having received by (i.c.v.) intracerebroventricular route either the ScAβ ("scrambled") peptide or the Aβ$_{25-35}$ peptide, and also by intra-cerebroventricular (i.c.v.) route an inert (V) vehicle or the PAT peptide. The evaluated parameter is the spontaneous alternation expressed as a percentage;

FIGS. 2A and 2B show the results obtained from passive avoidance test; the treated groups are identical to those of FIG. 1; in FIG. 2A is measured the latency time (in seconds) to enter into the dark compartment; and in FIG. 2B is measured the latency time to escape (in seconds);

FIG. 3 shows the results obtained from Y-maze test under the same conditions as for FIG. 1, except that the PAT peptide and the inert (V) vehicle are injected by intra-peritoneal (i.p.) route;

FIGS. 4A and 4B show the results obtained from passive avoidance test carried out such as for FIG. 2 except that the PAT peptide and the inert (V) vehicle are injected by intra-peritoneal (i.p.) route; in FIG. 4A is measured the latency time (in seconds) to enter into the dark compartment; and in FIG. 4B is measured the latency time to escape (in seconds).

FIGS. 5A and 5B show the results obtained from in vitro tests performed with rat primary dopaminergic neurons; in FIG. 5A is depicted the quantitative representation of the protective effect of PAT on the survival of TH-positive dopaminergic neurons exposed to 6-hydroxydopamine (6-OHDA) injury and pre-treated with vehicle (V), survival promoting brain derived neurotrophic factor (BDNF) or increasing concentrations of PAT (0.1 to 1000 nM). The evaluated parameter is the survival of TH-positive dopaminergic neurons (% of control condition, Ctrl). FIG. 5B show examples of microscopic aspect of neurons in control culture conditions (control), injured by 6-OHDA or pretreated with 10 nM PAT before 6-OHDA application are given.

FIGS. 6A and 6B show the results obtained from in vitro tests performed with rat primary GABAergic medium spiny neurons; in FIG. 6A is depicted the quantitative representation of the protective effect of PAT on the survival of GAD67-positive GABAergic neurons exposed to glutamate injury and pre-treated with vehicle (V), survival promoting brain derived neurotrophic factor (BDNF) or increasing concentrations of PAT (0.1 to 1000 nM). The evaluated parameter is the survival of GAD67-positive GABAergic neurons (% of control condition, Ctrl). FIG. 6B shows examples of microscopic aspect of medium spiny neurons in control culture conditions (control), injured by glutamate or pretreated with 10 nM PAT before glutamate application are given.

DETAILED DESCRIPTION OF THE INVENTION

In FIGS. 1 to 4B, one-way ANOVA followed by Dunnett's post hoc test was applied to the results: (*) means that the results are significant with a probability of <0.0001; (**) with a $p<0.01$ vs. ScAβ+V treatment group; (#) with a $p<0.05$ vs. (Aβ25-35+V) treatment group and (##) with a $p<0.01$ vs. (Aβ25-35+V) treatment group. In FIGS. 5A-5B and 6A-6B, statistical significance was determined by applying one-way ANOVA followed by Dunnett's test to the results: (*) means that the results were significant with a probability of <0.005 vs. 6-OHDA or glutamate condition respectively.

Example 1

Alzheimer's Model in Mice—Spontaneous Alternation Test

Experimental Protocol

The Swiss OF-1 (Depré, St Doulchard, France) mice were 7-9 weeks old from and weigh 32±2 g. They were dispatched into several groups and placed in plastic cages. They had free access to food and water, except during the behavioral experiments, and were maintained in an environment controlled (23±1° C., 40-60% of moisture) with light/darkness cycles of 12 hrs (light on at 8:00 am). The experiments were carried out between 9:00 am and 5:00 pm, in a room of experimentation. The mice were acclimated during 30 minutes before the beginning of the experiment. All the protocols followed the directives of the European Union dating of Nov. 24, 1986.

Treatment

The PAT peptide (5 μg) synthesized by Polypeptide (Denmark) was solubilized in distilled water and was administered by intra-peritoneal (i.p.) route in a volume of 100 μl (by 20 g of body weight) or by intra-cerebroventricular (i.c.v.) route at the same time as the amyloid peptide. The β [25-35] amyloid peptide called Aβ$_{25-35}$ and the Aβ25-35 "scrambled" peptide—called Sc.Aβ—were purchased from Genepep (France). They were resuspended in sterile distilled water at a concentration of 3 mg/ml and were preserved at 20° C. until their use. Before being injected, the peptides were subjected to an aggregation at 37° C. during 4 days. They are administered by i.c.v route in a final volume of 3 μl per mouse. The animals were tested at Day 7 after the injection.

In a first set of experiments, the mice received intracerebral (i.c.v.) administration of either water, or PAT nonapeptide (5 µg) at the same time than the ScAβ peptide or the Aβ$_{25-35}$ peptide (9 nmol). After a 7-days period, their performance in the spontaneous alternation test was evaluated. The numbers of animals per group were respectively 10 and 11. In a 2$^{nd}$ set of experiments, the same test was performed, except that the PAT peptide was administered by intraperitoneal (i.p.) route.

Test Course—Measured Parameters

We placed each mouse, which was not familiar with the device, at an end of a Y-maze (3 arms of 50 cm length and separated from 60°) and we let it move freely during 8 minutes. The number of entries in each arm, including the possible returns in the same arm, was counted visually. An entry was counted when the forelegs of the animal came at least 2 cm in the arm. An alternation was counted when an entry was made in all the 3 arms during successive tests. The number of total possible alternations was then the total number of entries minus 2 and the percentage of alternations was calculated as: (counted alternations/total of possible alternations)×100. The animals making less than 8 entries in 8 minutes were discarded from the experimental groups. No animal was excluded in this study. The compounds were administered 30 minutes before the session.

Results

The results are shown in FIG. 1 and FIG. 3 for the i.c.v. and i.p. administration routes, respectively.

As expected, when the Aβ$_{25-35}$ peptide was administered, the symptoms of Alzheimer's disease were induced. Administration of the control ScAβ peptide had no effect.

As expected, we observed that in FIG. 1 (i.c.v. route) when the ScAβ peptide was administered to the mice (which do not show any symptom of Alzheimer's disease) the co-administration of the PAT peptide had no effect. In contrast, co-administration of PAT peptide with the Aβ$_{25-35}$ peptide (thus the mice reproduce memory symptoms) exerted a significant neuroprotective effect on learning deficits induced by the Aβ$_{25-35}$ peptide.

In FIG. 3 (i.p. route), we also noticed a neuroprotective effect of the PAT peptide and this effect was very significant for the dose of PAT peptide between 1 and 3 mg/kg of body weight.

Example 2

Alzheimer's Model in Mice—Passive Avoidance Test

Experimental Protocol:

The information relative to the mice, the peptides, their administration and the treatment groups are similar to those of Example 1.

Test Course. Tested Parameters

The compounds were administered 30 minutes before the test. This test allowed the evaluation of the long term non-spatial memory. The device in the test consisted of an enlightened compartment having white PVC walls (with width/length/height dimensions of 15-20-15 cm respectively); an obscure compartment having black PVC walls (with same dimensions) and a grid on the ground. A trap door separated the 2 compartments. A lamp of 60 W was positioned 40 cm above and lightens the white compartment during the experiment. On the grid, random electric shocks of 0.3 mA were delivered to the mice legs during 3 seconds from a random power generator (Lafayette Instruments, USA).

The 1$^{st}$ phase of the experiment called "training" was carried out first. The trap door was closed at the beginning of the exercise. Each mouse was placed in the white compartment. The trap door was lifted after 5 seconds. When the mouse entered into the dark compartment and touched the grid with all its legs, the trap door was closed and the random electric shock was delivered on the legs during 3 seconds. The latency time before the entry into the dark compartment and the number of counts were recorded. The number of counts did not differ between the groups, indicating that the sensitivity to the electric shock was not affected by the type of administration route i.e. here i.c.v. or i.p. (not shown results). The animals for which the latency time was out the range of 3-30 seconds were discarded from the experiment. The attrition rates accounted for less than 2% of the animals and were independent of the treatment.

The 2$^{nd}$ phase of the experiment called "retention" was carried out 24 h after the 1$^{st}$ phase ("training"). Each mouse was placed again in the white compartment. The trap door was raised after 5 seconds. The latency time of entry into the dark compartment was recorded during a 300 seconds period. The number of entries and the time of escape (time spent going back into the white compartment) were measured during a 300 seconds period.

Results

The results are presented in FIGS. 2 (2A and 2B) for the administration by i.c.v. route; and in FIGS. 4 (4A and 4B) for the administration by i.p. route.

The FIG. 2—administration by i.c.v. route—shows clearly that the injection of the PAT peptide (5 µg) by i.c.v. route in mice having received the Aβ$_{25-35}$ peptide (the latter reproducing training deficits) improved the 2 criteria tested when they were compared to mice having received water distilled (V) only. Thus, by using this animal model of Alzheimer's disease, it was demonstrated that the PAT peptide presented at a significant neuroprotective effect.

Again, in FIG. 4—administration by i.p. route—a neuroprotective effect of PAT peptide was observed. As in the spontaneous alternation test, the neuroprotective effect of the PAT was observable for a dose higher than 0.3 mg/kg of body weight.

Thus, the use of the 2 animal models of Alzheimer's disease shows that the PAT peptide is an interesting and promising candidate to treat and prevent cerebral lesions related to the training deficit.

Example 3

Cellular Model of Parkinson's Disease—Survival of Rat Primary Dopaminergic Neurons after 6-Hydroxydopamine Injury 6-hydroxydopamine (6-OHDA) is a selective catecholaminergic neurotoxin that is not only used as a pharmacological agent able to trigger PD-like stigmata (Sauer H. and Oertel W H Neuroscience 1994; 59: 401 and Cass W A et al. Brain Res. 2002; 938: 29) but also likely corresponds to a natural dopaminergic catabolite that accumulates in PD-affected brains and that appears to strongly contribute to this pathology (Jellinger K. et al. J. Neural. Transm. 1995; 46: 297). For this reason, 6-OHDA-induced dopaminergic neurotoxicity in mice is widely used as a model for PD research. Because 6-OHDA also induces neurodegeneration of dopaminergic neurons in vitro, it provides a useful model of PD. In this in vitro test mesencephalic dopaminergic neurons are exposed to 6-OHDA injury. Neuroprotective effect of a test compound is evaluated by pre-incubating the mesencephalic neurons for 1 h before the 6-OHDA application. After 24 h of intoxication, viable dopaminergic neurons are visualized and quantified by staining with a monoclonal Anti-Tyrosine Hydroxylase (TH) antibody. Tyrosine Hydroxylase is the first and rate-limiting enzyme involved in the biosynthesis of catecholamines like dopamine and norepinephrin from Tyrosine and has a key role in the physiology of adrenergic neurons. Tyrosine hydroxylase is commonly used as a marker for dopaminergic neurons, which is particularly relevant for research in Parkinson's disease. Brain derived neurotrophic factor (BDNF) is used as a positive control that has been shown to reduce the 6-OHDA-induced neurodegeneration in vitro (Riveles K et al. Neurotoxicology 2008; 29: 421).

Experimental Protocol

Rat dopaminergic neurons were cultured as described by Schinelli et al. J. Neurochem. 1988; 50: 1900 and Visanji N P et al. FASEB J. 2008; 22: 2488. Briefly, the midbrains obtained from 15-day old rat embryos (Janvier, France) were dissected under a microscope. The embryonic midbrains were removed and placed in ice-cold medium of Leibovitz (L15) containing 2% of Penicillin-Streptomycin (PS) and 1% of bovine serum albumin (BSA). The ventral portion of the mesencephalic flexure, a region of the developing brain rich in dopaminergic neurons, was used for the cell preparations.

The midbrains were dissociated by trypsinisation for 20 min at 37° C. (Trypsin EDTA 1X). The reaction was stopped by the addition of Dulbecco's modified Eagle's medium (DMEM) containing DNAase I grade II (0.1 mg/ml) and 10% of fetal calf serum (FCS). Cells were mechanically dissociated by 3 passages through a 10 ml pipette. Cells were then centrifuged at 180×g for 10 min at +4° C. on a layer of BSA (3.5%) in L15 medium. The supernatant was discarded and the cell pellets were re-suspended in a defined culture medium consisting of Neurobasal (Invitrogen) supplemented with B27 (2%), L-glutamine (2 mM) and 2% of PS solution and 10 ng/ml of BDNF and 1 ng/ml of Glial-Derived Neurotrophic Factor (GDNF). Viable cells were counted in a Neubauer cytometer using the trypan blue exclusion test. The cells were seeded at a density of 40 000 cells/well in 96 well-plates (pre-coated with poly-L-lysine) and maintained in a humidified incubator at 37° C. in 5% CO2/95% air atmosphere. Half of the medium was changed every 2 days with fresh medium.

Treatment

On day 6 of culture, the medium was removed. The PAT peptide (10 mg) synthesized by Polypeptide (Denmark) was solubilized in distilled water. PAT (concentrations ranging from 0.1 nM to 1 µM) or BDNF (50 ng/mL i.e. 2 nM) were solved in culture medium (containing 0.1% DMSO) and then pre-incubated with mesencephalic neurons for 1 hour before the 6-OHDA application. One hour after test compound incubation, 6-OHDA was added to a final concentration of 20 µM diluted in culture medium still in presence of compound or BDNF for 24 hours. Each condition was tested on one culture mesencephalic dopaminergic neurons but 6 independent replicates.

End Point Evaluation: Measurement of Total Number of TH-Positive Neurons After 24 hours of intoxication, cells were fixed by a solution of 4% paraformaldehyde in PBS, pH=7.3 for 20 min at room temperature. The cells were washed again twice in PBS, permeabilized and non-specific sites were blocked with a solution of PBS containing 0.1% of saponin and 1% FCS for 15 min at room temperature. Then, cells were incubated with monoclonal anti-tyrosine hydroxylase (TH) antibody produced in mouse at dilution of 1/10,000 in PBS containing 1% FCS, 0.1% saponin, for 2 hours at room temperature. These antibodies were revealed with Alexa Fluor 488 goat anti-mouse IgG at the dilution 1/800 in PBS containing 1% FCS, 0.1% saponin, for 1 h at room temperature.

For each condition, 20 pictures per well were acquired (representing 80% of the total surface of the well) using ImageXpress (Molecular device) equipped with a LED at 10× magnification. All images were acquired with the same conditions. The number of TH-positive neurons was automatically analyzed using MetaXpress software (Molecular device). Data were expressed in percentage of control conditions (no intoxication, no 6-OHDA=100%) in order to express the 6-OHDA injury. All values were expressed as mean+/−SEM (s.e.mean) (n=6 wells per condition per culture).

Results

The results are depicted in FIGS. 5A and 5B. FIG. 5A shows quantitative representation of the effect of PAT on the survival of TH-positive dopaminergic neurons injured by 6-OHDA. FIG. 5B shows examples of microscopic aspect of mesencephalic neurons in control culture conditions, injured by 6-OHDA or pretreated with 10 nM PAT before 6-OHDA application.

As previously shown in the literature, the survival of TH-positive dopaminergic neurons exposed to 6-OHDA was reduced by 31% compared to cells maintained in control culture conditions. Pretreatment with BNDF neurotrophic factor fully protected TH-positive neurons from 6-OHDA-induced cell death.

Pre-incubation of dopaminergic neurons with PAT resulted in a dose-dependent protection against 6-OHDA injury. 100% survival levels were achieved with a concentration of PAT as low as 10 nM. Under these conditions PAT was as potent as BNDF.

The potent neuroprotective activity of PAT was obvious when looking at the microscopic aspect of dopaminergic neurons as illustrated in FIG. 5B. Exposure to 6-OHDA resulted in a strong reduction of TH-positive neurons per well compared to control culture conditions due to cell death. Treatment with PAT restored the number of viable TH-positive neurons per well to a level similar to control conditions.

Example 4

Cellular Model of Huntington's Disease— Survival of Rat Primary Gabaergic Medium Spiny Neurons after Glutamate Injury GABAergic medium spiny neurons (MSNs) in the striatum represent the mostly affected cell population in HD brain. Being the main neuronal cell type of the striatum (85% in humans), GABAergic MSNs play a central role in the clinical manifestation of HD. GABA is viewed as the neurotransmitter that inhibits spontaneous involuntary movements, therefore loss of GABAergic MSNs is responsible for chorea development and other involuntary movements. The exquisite vulnerability of MSNs of striatum to degeneration in HD is caused by glutamate excitotoxicity that leads to neuronal dysfunction and death. Excessive activation of NMDA glutamate receptors is observed in post-mortem HD brain tissue (Kumar P. et al. Pharmacol. Rep. 2010; 62: 1). Because glutamate is toxic to GABAergic striatal neurons in vitro, it provides a useful model of HD (Freese A et al. Brain Res. 1990; 521: 254). In this in vitro test, GABAergic MSNs are exposed to glutamate injury. Neuroprotective effect of a test compound is evaluated by pre-incubating MSNs for 1 h before the glutamate application. After 24 h of intoxication, viable GABAergic neurons are visualized and quantified by staining with a monoclonal anti-Glutamic Acid Decarboxylase antibody (specific for isoform GAD67). Glutamic acid decarboxylase is the first and rate-limiting enzyme involved in the biosynthesis of GABA from glutamic acid in higher brain regions. Brain derived neurotrophic factor (BDNF) is used as a positive control given that it has been identified as a factor required for the maturation and survival of MSNs (Ivkovic S et al. J. Neurosci. 1999; 19: 5409).

Experimental Protocol:

The information relative to the preparation of mesencephalic rat neurons, the culture conditions and treatment of cells are similar to those of Example 3.

Treatment

On day 13 of culture, the medium was removed. The PAT peptide (10 mg) synthesized by Polypeptide (Denmark) was solubilized in distilled water. PAT (concentrations ranging from 0.1 nM to 1 µM) or BDNF (50 ng/mL i.e. 2 nM) were solved in culture medium (containing 0.1% DMSO) and then pre-incubated with MSNs for 1 hour before the glutamate application. One hour after test compound incubation, glutamate was added to a final concentration of 10 µM diluted in culture medium still in presence of compound or BDNF for 20 min. After 20 min, glutamate was washed and fresh culture medium with BNDF or test compound was added for additional 24 h. Each condition was tested on one culture mesencephalic GABAergic neurons but 6 independent replicates.

End Point Evaluation: Measurement of Total Number of GAD67 Positive Neurons

After 24 hours of intoxication, cells were fixed with a cold solution of ethanol (95%) in acetic acid (5%) for 5 min. The cells were washed again twice in PBS, permeabilized and non-specific sites were blocked with a solution of PBS containing 0.1% of saponin and 1% FCS for 15 min at room temperature. Then, cells were incubated with monoclonal anti-GAD67 antibody produced in mouse at dilution of 1/200 in PBS containing 1% FCS, 0.1% saponin, for 2 hours at room temperature. These antibodies were revealed with Alexa Fluor 488 goat anti-mouse IgG at the dilution 1/400 in PBS containing 1% FCS, 0.1% saponin, for 1 h at room temperature.

For each condition, 30 pictures per well were acquired (representing 80% of the total surface of the well) using ImageXpress (Molecular device) equipped with a LED at 20× magnification. All images were acquired with the same conditions. The number of GAD67-positive neurons was automatically analyzed using MetaXpress software (Molecular device). Data were expressed in percentage of control conditions (no intoxication, no glutamate=100%) in order to express the glutamate injury. All values were expressed as mean+/−SEM (s.e. mean) (n=6 wells per condition per culture).

Results

The results are depicted in FIGS. 6A and 6B. FIG. 6A shows quantitative representation of the effect of PAT on the survival of GAD67-positive neurons injured by glutamate. FIG. 6B shows examples of microscopic aspect of GAD67-positive GABAergic MSNs in control culture conditions, injured by glutamate or pretreated with 10 nM PAT before glutamate application.

As expected, the survival of GAD67-positive MSN exposed to glutamate was reduced by 38% compared to cells maintained in control culture conditions. Pretreatment with BNDF neurotrophic factor protected GAD67-positive neurons from glutamate-induced cell death to some extent (81% cell survival).

Pre-incubation of GABAergic neurons with PAT resulted in a dose-dependent protection against glutamate injury. Survival levels above 90% were achieved with concentrations of PAT starting from 10 nM. PAT was in average more potent than BNDF in tested conditions.

The potent neuroprotective activity of PAT was obvious when looking at the microscopic aspect of GABAergic neurons as illustrated in FIG. 6B. Exposure to glutamate resulted in a strong reduction of GAD67-positive neurons per well compared to control culture conditions due to cell death. Treatment with PAT restored the number of viable GAD67-positive neurons per well to a level similar to control conditions.

Thus the use of established cellular models of Parkinson's and Huntington's disease shows that PAT exerts a potent protective effect on injured neurons. In addition, PAT reduces cognitive decline in a mouse model of Alzheimer's disease. All together this peptide proves to be an interesting and promising candidate to treat and prevent neurodegenerative disorders with highly unmet medical needs.

---

---

The invention claimed is:

1. A method of treating a neurodegenerative disease, comprising administering an effective amount of a PAT nonapeptide of formula (I): EAKSQGGSD (SEQ ID NO: 1), or a pharmaceutically acceptable salt thereof, to a subject in need thereof wherein the neurodegenerative disease is selected from the group consisting of Alzheimer's disease, Parkinson's disease, Huntington's disease, and amyotrophic lateral sclerosis.

2. The method according to claim 1, wherein the neurodegenerative disease is Alzheimer's disease.

3. The method according to claim 1, wherein the neurodegenerative disease is Parkinson's disease.

4. The method according to claim 1, wherein the neurodegenerative disease is Huntington's disease.

5. The method according to claim 1, wherein the neurodegenerative disease is amyotrophic lateral sclerosis.

6. The method according to claim 1, wherein the PAT nonapeptide is administered by parenteral route.

7. The method according to claim 1, wherein the PAT nonapeptide is administered by subcutaneous, intra-peritoneal, intravenous or intranasal administration, or by sublingual orodispersible tablet.

8. The method according to claim 1, wherein the PAT nonapeptide is administered in a dose ranging between 0.1 and 50 mg.

9. The method according to the claim 8, wherein the dose is in a range between 1 and 10 mg.

10. The method according to claim 1, wherein at least one amino-acid of the PAT nonapeptide has the D configuration.

11. The method according to claim 1, wherein the subject is a human.

* * * * *